(12) United States Patent
Curry

(10) Patent No.: US 8,092,476 B2
(45) Date of Patent: Jan. 10, 2012

(54) ADJUSTABLE CAP AND LANCING DEVICE AND METHOD OF USE

(75) Inventor: Samuel Mason Curry, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 366 days.

(21) Appl. No.: 12/191,824

(22) Filed: Aug. 14, 2008

(65) Prior Publication Data

US 2010/0042129 A1   Feb. 18, 2010

(51) Int. Cl.
*A61B 17/14* (2006.01)
(52) U.S. Cl. ............................................. 606/181
(58) Field of Classification Search .............. 606/172, 606/181, 182, 183; 600/583; 604/136, 137, 604/138, 139
See application file for complete search history.

(56) References Cited

U.S. PATENT DOCUMENTS

| | | | |
|---|---|---|---|
| 4,375,815 A | 3/1983 | Burns |
| 4,462,405 A | 7/1984 | Ehrlich |
| 4,637,403 A | 1/1987 | Garcia et al. |
| 4,990,154 A | 2/1991 | Brown et al. |
| 5,423,847 A | 6/1995 | Strong et al. |
| 5,540,709 A | 7/1996 | Ramel |
| 5,613,978 A | 3/1997 | Harding |
| 5,628,764 A | 5/1997 | Schraga |
| 5,666,966 A | 9/1997 | Horie et al. |
| 5,857,983 A | 1/1999 | Douglas et al. |
| 5,873,887 A | 2/1999 | King et al. |
| 5,879,311 A | 3/1999 | Duchon et al. |
| 5,879,367 A | 3/1999 | Latterell et al. |
| 5,916,230 A | 6/1999 | Brenneman et al. |
| 5,951,492 A | 9/1999 | Douglas et al. |
| 5,951,493 A | 9/1999 | Douglas et al. |
| 5,964,718 A | 10/1999 | Duchon et al. |
| 6,056,701 A | 5/2000 | Duchon et al. |
| 6,066,103 A | 5/2000 | Duchon et al. |
| 6,071,250 A | 6/2000 | Douglas et al. |

(Continued)

FOREIGN PATENT DOCUMENTS

WO    WO2005046477    5/2005

OTHER PUBLICATIONS

PCT International Search Report (Date of Mailing: Nov. 2, 2009); PCT/US2009/053646, filed Aug. 13, 2009.

*Primary Examiner* — Ryan Severson
*Assistant Examiner* — Jonathan W Miles
(74) *Attorney, Agent, or Firm* — Young Basile

(57) ABSTRACT

Disclosed are cap embodiments each comprising a body having a skin-engaging end defining a piercing aperture, a lancet receiver, and an intermediate member. A first cam path is located on one of the lancet receiver and the intermediate member, and a first cam follower is located on the other of the lancet receiver and the intermediate member that engages the first cam path. A second cam path is located on one of the cap body and the intermediate member, and a second cam follower is located on the other of the cap body and the intermediate member that engages the second cam path. The first and second cam paths are configured such that rotation of the intermediate member by an actuating mechanism causes the cap body to move forward and rearward and the lancet receiver to move forward and rearward. Also disclosed are lancing devices and methods of use.

20 Claims, 6 Drawing Sheets

U.S. PATENT DOCUMENTS

| | | |
|---|---|---|
| 6,086,545 A | 7/2000 | Roe et al. |
| 6,156,050 A | 12/2000 | Davis et al. |
| 6,210,420 B1 | 4/2001 | Mauze et al. |
| 6,319,210 B1 | 11/2001 | Douglas et al. |
| 6,332,871 B1 | 12/2001 | Douglas et al. |
| 6,346,114 B1 | 2/2002 | Schraga |
| 6,451,040 B1 | 9/2002 | Purcell |
| 6,464,649 B1 | 10/2002 | Duchon et al. |
| 6,491,709 B2 | 12/2002 | Sharma et al. |
| 6,530,937 B1 | 3/2003 | Schraga |
| 6,645,219 B2 | 11/2003 | Roe |
| 2002/0010406 A1 | 1/2002 | Douglas et al. |
| 2002/0022789 A1 | 2/2002 | Perez et al. |
| 2002/0029058 A1 | 3/2002 | Levaughn et al. |
| 2002/0082521 A1 | 6/2002 | Sharma et al. |
| 2002/0188223 A1 | 12/2002 | Perez et al. |
| 2003/0050655 A1 | 3/2003 | Roe et al. |
| 2003/0195540 A1 | 10/2003 | Moerman |
| 2004/0073140 A1 | 4/2004 | Douglas et al. |
| 2004/0162573 A1 | 8/2004 | Kheiri |
| 2004/0254599 A1 | 12/2004 | Lipoma et al. |
| 2005/0085839 A1 | 4/2005 | Allen et al. |
| 2005/0096686 A1 | 5/2005 | Allen |
| 2005/0215925 A1 | 9/2005 | Chan |
| 2006/0184189 A1 | 8/2006 | Olson et al. |
| 2006/0271084 A1 | 11/2006 | Schraga |
| 2006/0287664 A1 | 12/2006 | Grage, Jr. et al. |
| 2007/0055298 A1 | 3/2007 | Uehata et al. |
| 2007/0083222 A1 | 4/2007 | Schraga |
| 2008/0027474 A1 | 1/2008 | Curry et al. |
| 2009/0043326 A1 | 2/2009 | Zhong |

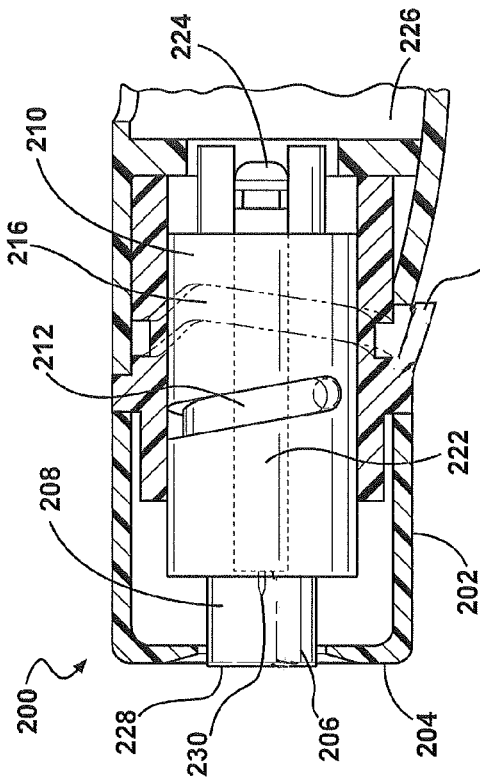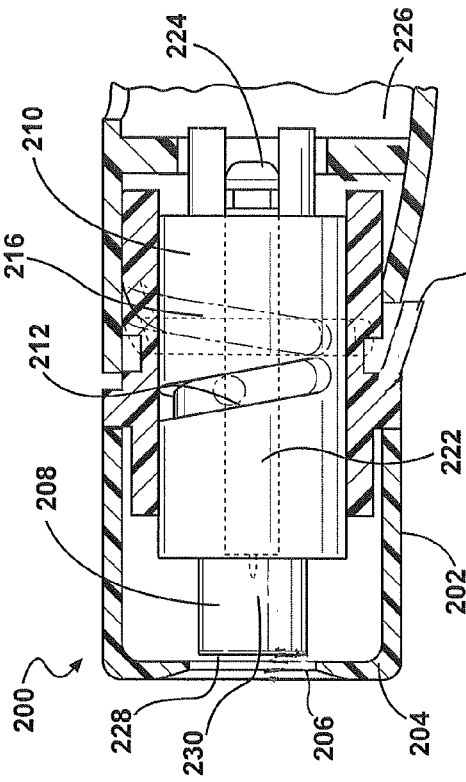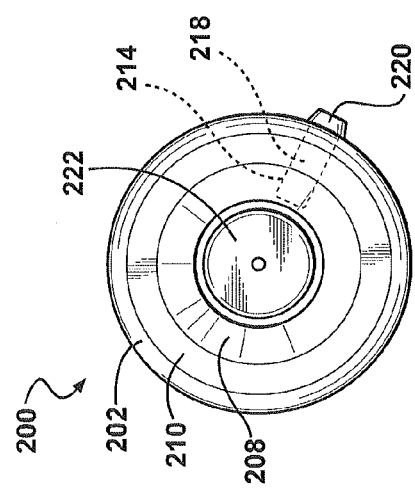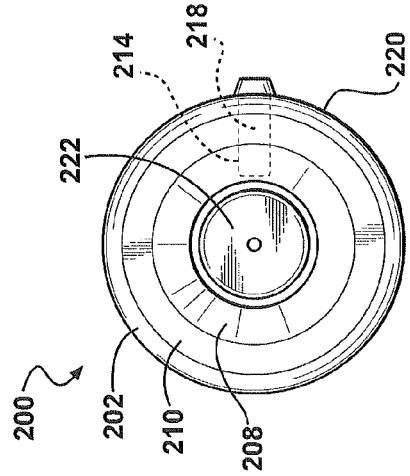

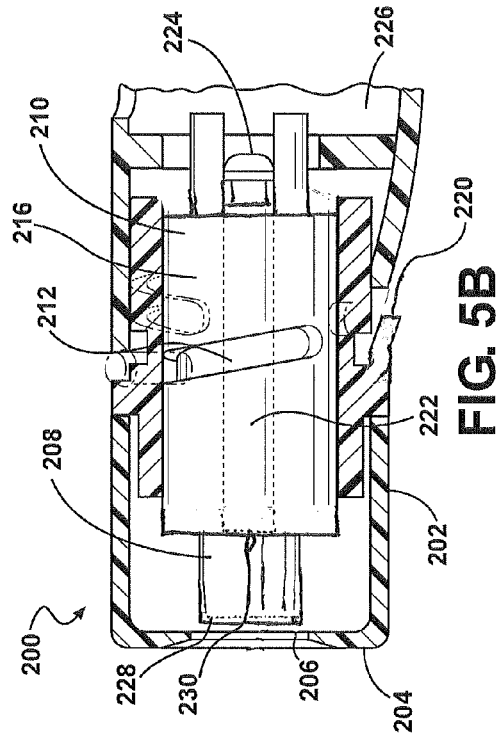
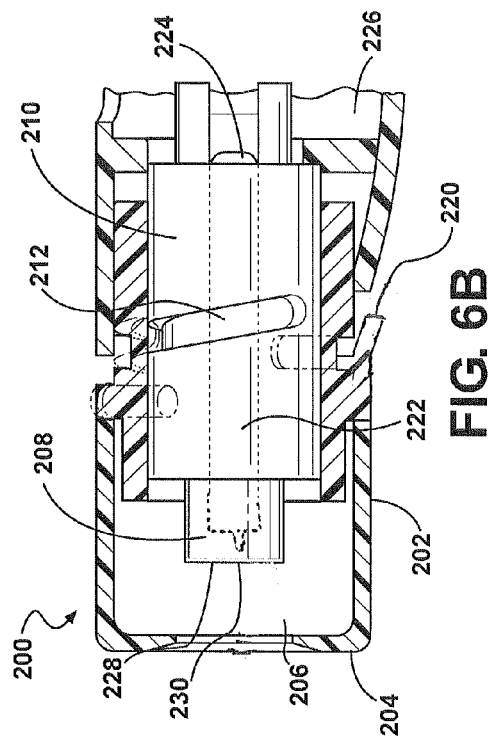
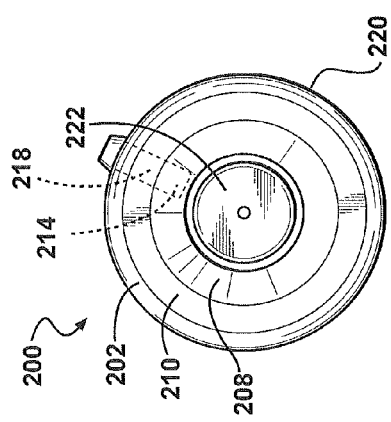
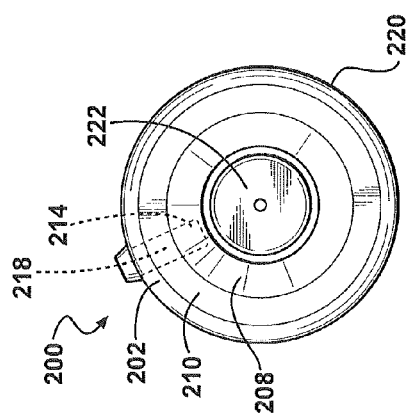

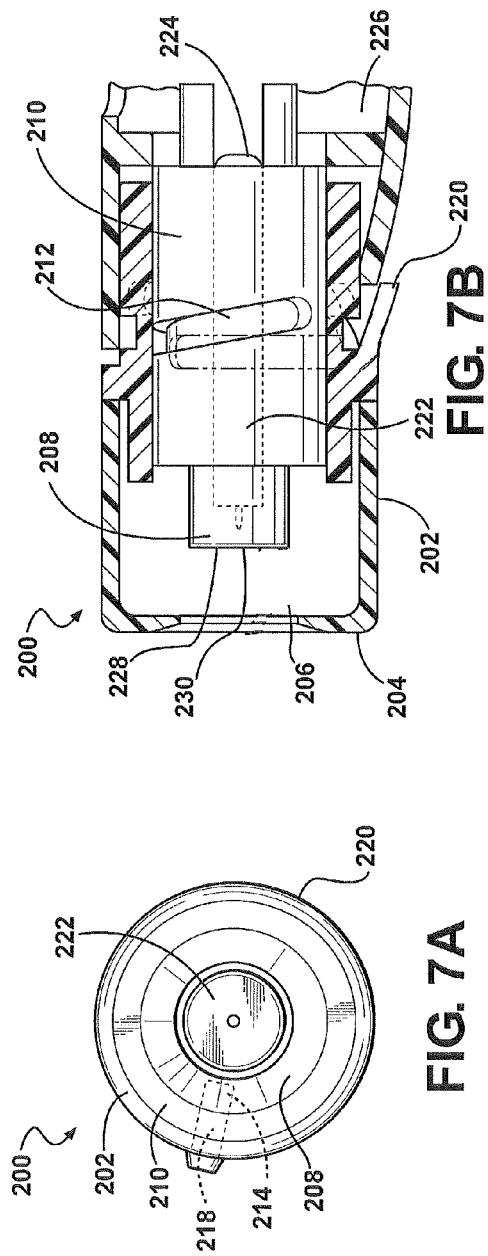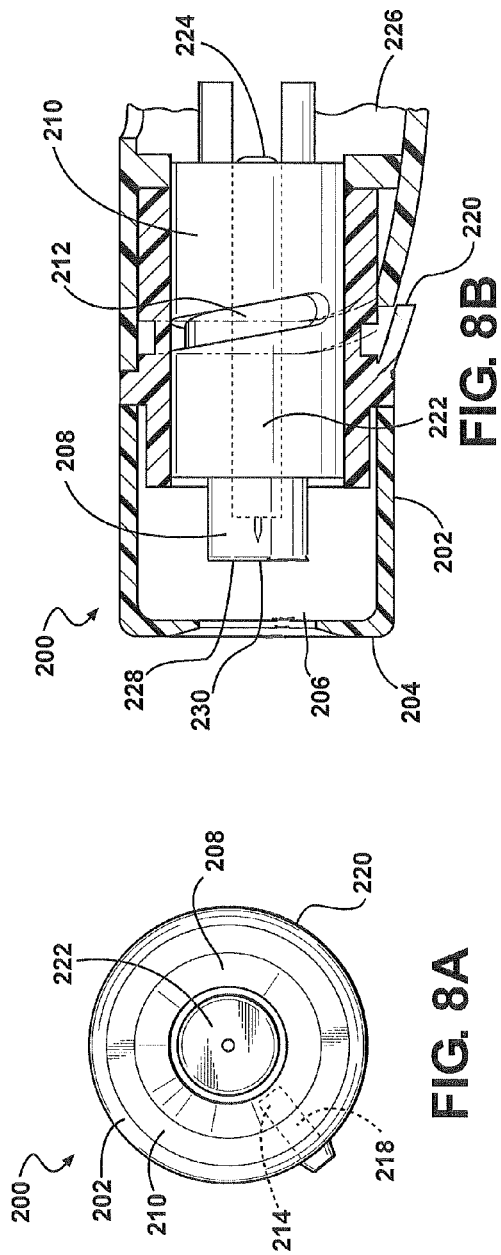

ADJUSTABLE CAP AND LANCING DEVICE AND METHOD OF USE

BACKGROUND

Lancing devices are typically handheld units that permit users to draw blood for testing and diagnostic purposes. These devices include a housing with a piercing aperture, a lancet and a firing mechanism. The firing mechanism typically includes a spring or other biasing means which can be cocked either by insertion of the lancet or by pulling a cocking handle, for example. Once the lancing device is cocked, it is placed against the user's skin, often the fingertip. The user can then press a trigger to actuate the firing mechanism, which momentarily drives the sharp tip of lancet through the piercing aperture to puncture the user's skin and draw blood. When the lancing operation is complete, the user can press a second actuator to eject the lancet for removal and disposal. A consideration in the design of both lancets and lancet devices is to minimize parts and thus minimize cost of production.

Another consideration in the design of lancets is to minimize the discomfort experienced by users during the lancing process. To this end, some lancing devices include mechanisms to adjust the distance that the lancet sharp protrudes through the piercing aperture, thus regulating the depth that the lancet penetrates the user's skin. In some cases, these depth adjustment mechanisms include adjustable stops that limit the forward movement of the lancet during firing. In other cases, a lancet holder is moved axially within a lancing device housing to move the needle closer to or farther away from the piercing aperture, thus adjusting penetration depth.

Lancing devices can draw blood from a user's fingertip or other body part. A fingertip is a good testing site because it contains a large number of blood vessels and it is therefore easy to draw an adequate quantity of blood from the fingertip. However, fingertips are also sensitive and users who must frequently draw blood samples may experience discomfort from repeated sampling of the fingertips. Therefore, some users also perform lancing operations on parts of the body, and this is known as alternate site testing or alternate site incision, also known as "AST."

To effectively draw blood from an alternate site, it is helpful to have the needle penetrate the skin more deeply. It is also helpful to have a relatively wide piercing aperture. A wider piercing aperture acts as an expression ring by allowing the skin to pucker into the aperture's opening and by compressing a wider area of skin around the incision. When skin protrudes through the aperture into the housing, it is also more deeply penetrated by the lancet.

Another consideration in the design of lancing devices is to avoid accidental needle pricks when inserting and removing lancets from the lancing device. To this end, lancets include safety features such as frangible tabs which cover the needle sharp prior to insertion in the lancing device. Once the lancet is inserted, the use can break off and remove the frangible tab. Some lancets also include sleeves coaxially mounted to the main body of the lancet. The sleeve can be positioned so that it protectively encloses the needle sharp. During the lancing operation, the main body of the lancet slides through the sleeve to expose the lancet sharp. After removal of the lancet, however, the sleeve can be locked in its protective position, reducing the likelihood that a person handling the use lancet will prick himself or herself.

Another consideration in the design of lancing systems is the ease with which a lancet can be inserted into the lancing device. It is known that when a lancet is inserted into a lancing device, the force of the insertion can be used to cock the device. However, if the device is already cocked, and a lancet was to be inserted, there is some risk that the device would discharge during the insertion process and the user would be accidentally pricked. It is also known to insert the lancet into the lancet device when the cap of the device is removed.

SUMMARY

Caps and lancing devices with adjustable modes are provided along with methods of use. In accordance with some embodiments of the invention, a cap is disclosed for use with a lancing device having a housing and a lancet firing mechanism disposed therein. The cap comprises a cap body having a skin-engaging end that defines a piercing aperture, a lancet receiver movably mounted in the cap body and an intermediate member. A first cam path is located on one of the lancet receiver and the intermediate member, and a first cam follower is located on the other of the lancet receiver and the intermediate member that engages the first cam path. A second cam path is located on one of the cap body and the intermediate member, and a second cam follower is located on the other of the cap body and the intermediate member that engages the second cam path. The first and second cam paths are configured such that rotation of the intermediate member by an actuating mechanism causes the cap body to move forward and rearward and the lancet receiver to move forward and rearward.

In accordance with other embodiments of the invention, a method of using a cap of a lancing device is disclosed, wherein the cap has a body, a skin-engaging end defining a piercing aperture, an intermediate member and a lancet receiver movably disposed therein. The method comprises adjusting an effective size of the piercing aperture by moving the lancet receiver between a forward position and a rearward position, wherein an end of the lancet receiver is circumscribed by and is substantially co-planar with the skin-engaging end when the lancet receiver is in the forward position, with the end of the lancet receiver defining the piercing aperture. The lancet receiver is positioned sufficiently spaced apart from the piercing aperture to permit skin to pucker through the piercing aperture during lancing when in the rearward position. A penetration depth of a lancet is adjusted by moving the cap body forward and rearward when the lancet receiver is in either of the forward and rearward positions. Adjusting the effective size comprises moving a first cam follower located on one of the lancet receiver and the intermediate member with an actuating mechanism along a first cam path located on the other of the lancet receiver and the intermediate member. Adjusting the penetration depth comprises moving a second cam follower located on one of the cap body and the intermediate member with the actuation member along a second cam path on the other of the cap body and the intermediate member.

In accordance with yet other embodiments of the invention, a lancing device is disclosed including a cap having a body, a skin-engaging end defining a piercing aperture, a lancet receiver disposed in the cap, an intermediate cap member, a housing and a lancet firing mechanism disposed in the housing. The lancing device comprises a first cam path on one of the lancet receiver and the intermediate member, and a first cam follower on the other of the lancet receiver and the intermediate member that engages the first cam path. A second cam path is located on one of the cap body and the intermediate member, and a second cam follower is located on the other of the cap body and the intermediate member that engages the second cam path. The first and second cam paths are configured such that rotation of the intermediate member by an actuating mechanism causes the cap to move forward and rearward and the lancet receiver to move forward and rearward.

BRIEF DESCRIPTION OF THE DRAWINGS

The description herein makes reference to the accompanying drawings wherein like reference numerals refer to like parts throughout the several views, and wherein:

FIGS. 3A and B are perspective views of an embodiment disclosed herein in a first position;

FIGS. 4A and B are perspective views of an embodiment disclosed herein in a second position;

FIGS. 5A and B are perspective views of an embodiment disclosed herein in a third position;

FIGS. 6A and B are perspective views of an embodiment disclosed herein in a fourth position;

FIGS. 7A and B are perspective views of an embodiment disclosed herein in a fifth position;

FIGS. 8A and B are perspective views of an embodiment disclosed herein in a sixth position;

DETAILED DESCRIPTION OF THE EMBODIMENTS

Figure 1:
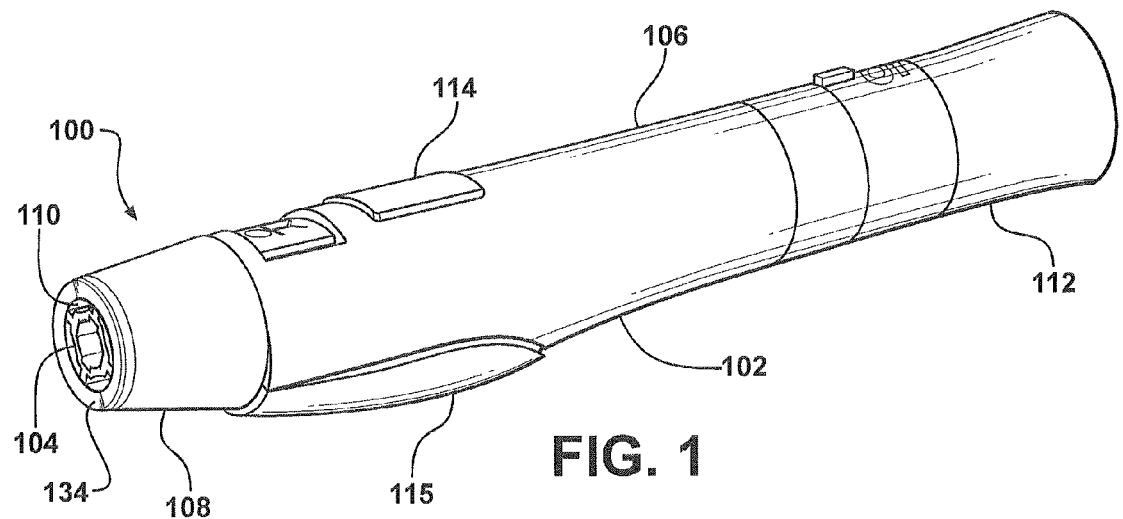
FIG. 1 is a perspective view of an example of a lancing device, including a removable lancet inserted therein.

Lancing systems are used to draw a sample of blood or other bodily fluid from the body such as for diagnostic purposes. Typical lancing systems share similar functional elements. Referring to FIG. 1, an example of a lancing system 100 is illustrated, including a lancing device 102 and removable lancet 104. The lancing system 100 is operated by a user The lancing device 102 includes a housing 106 with a skin-engaging cap 108 having a piercing aperture 110, a cocking handle 112 used to cock a lancet firing mechanism, a trigger 114 for firing the lancet firing mechanism, and perhaps an ejection slide 115 to eject the lancet 104 from the lancing device 102 after use.

Figure 2:
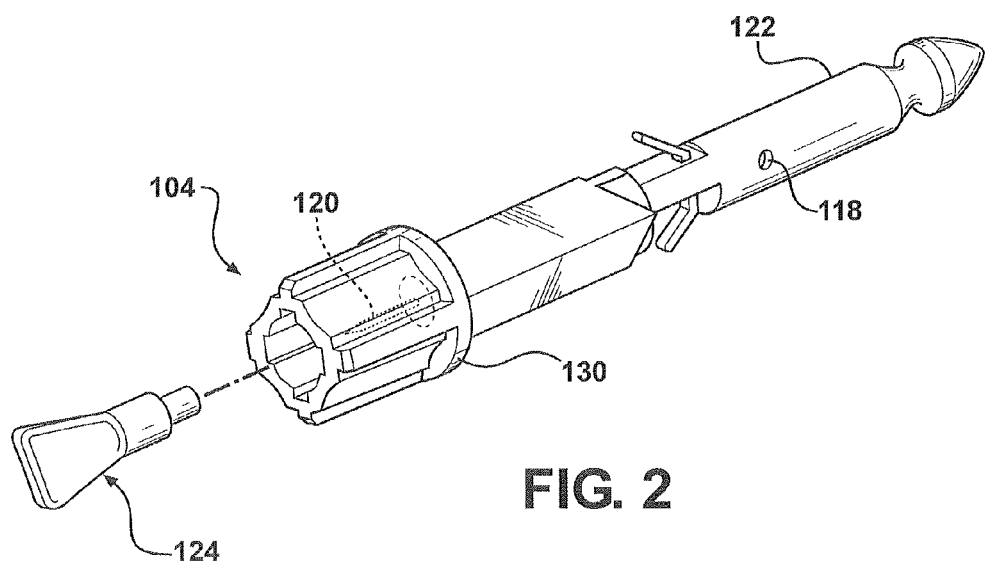
FIG. 2 is a perspective view of a lancet that can be used with the lancing device of FIG. 1, including a removable tab and a sleeve in an extended position to protectively surround the lancet's needle.

As shown in FIG. 2, an example of a lancet 104 includes a needle 118 whose length (excluding a sharp tip 120) is encased in an elongated lancet body 122. A removable tab 124 can be frangibly attached to the front end of the lancet body 122. A sleeve 130 slides axially over a portion of the lancet body 122 between a forward position (as shown in FIG. 2), in which it protectively surrounds the sharp tip 120 of the needle 118, and a rearward position in which a portion of the sharp tip 120 protrudes beyond the front end of the sleeve 130.

The lancing system 100 can also be used in a kit which can include test strips and an analyzer. After the lancing system 100 is operated to draw blood, the user can apply the bead of blood to the test strip and insert the test strip into the analyzer for assessment of blood composition, such as levels of glucose.

Figure 11:
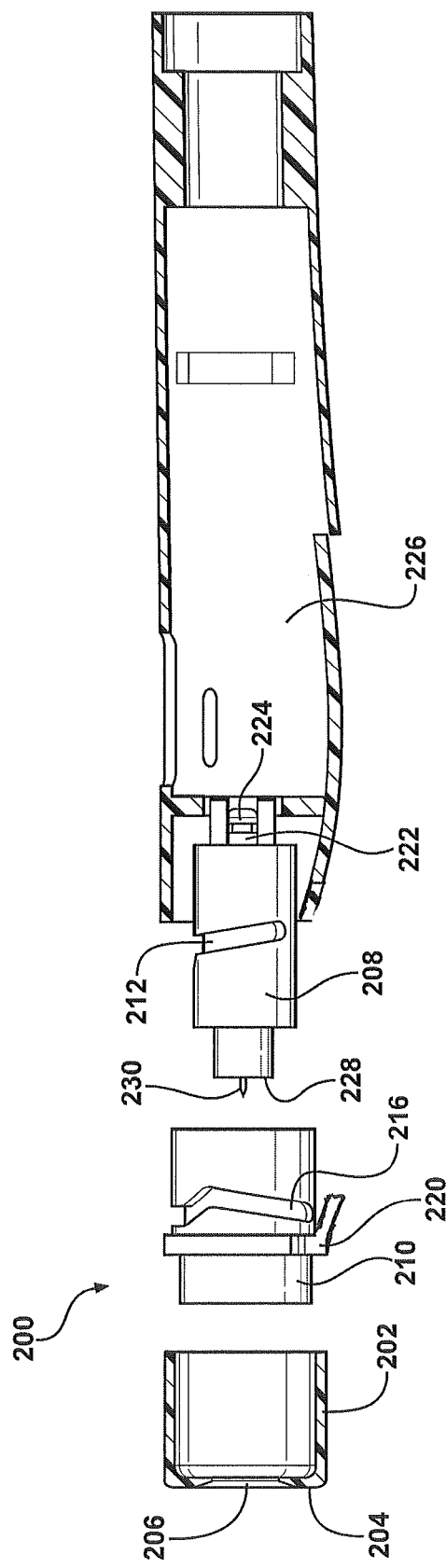
FIG. 11 is an expanded view of a lancing device having the cap of the first embodiment

In accordance with one embodiment of the invention, a cap 200 for use with a lancing device such as that described with reference to FIG. 1 is disclosed. Referring to FIGS. 3A-8B, the cap 200 comprises a cap body 202 having a skin-engaging end 204 that defines a piercing aperture 206, a lancet receiver 208 movably mounted in the cap body 202, and an intermediate member 210. A first cam path 212 is located on one of the lancet receiver 208 and the intermediate member 210, and a first cam follower 214 is located on the other of the lancet receiver 208 and the intermediate member 210, the first cam follower 214 engaging the first cam path 212. A second cam path 216 is located on one of the cap body 202 and the intermediate member 210, and a second cam follower 218 is located on the other of the cap body 202 and the intermediate member 210 and engages the second cam path 216. The first and second cam paths 212, 216 are configured such that rotation of the intermediate member 210 by an actuating mechanism 220 causes the cap body 202 to move forward and rearward and the lancet receiver 208 to move forward and rearward. FIG. 11 is an expanded view of a lancing device having the cap 200 of the first embodiment.

In this specification, unless otherwise provided, the term "forward" means away from the housing of the lancing device along the longitudinal axis of the housing, and "rearward" means towards the housing of the lancing device along the longitudinal axis A of the housing, shown in FIG. 3B.

A lancet 222 is loaded into the lancet receiver 208 through the piercing aperture 206. The lancet receiver 208 releasably engages the lancet 222 or the lancet sleeve if the lancet is of such a type. The lancet receiver 208 is generally tubular in construction defining an elongated inner chamber therein that is sized and configured to receive the lancet 222. For example, the diameter of the lancet receiver 208 can range from 3 mm to less than 6 mm. The elongated interior chamber is configured for mating engagement with the external contours of the lancet 222 and/or lancet sleeve. When the lancet 222 is fully inserted into the lancet receiver 208, an end 224 of the lancet 222 will engage with a lancet firing mechanism (not shown) disposed within the housing 226 that is configured to move the lancet 222 between a cocked position and an extended position to lance the user's skin. Lancet firing mechanisms are known to those skilled in the art and will not be described in detail here.

As will be explained below, the cap 200 can be moved between different operating positions, shown in FIGS. 3A-8B. For example, the cap 200 can be operated in both a finger mode and an alternate site test mode (hereinafter "AST mode") via use of the first cam path 212 and cam follower 214. In AST mode, the cap 200 is configured for use with fleshy parts of the body such as a thigh or forearm. In finger mode, the cap 200 is configured for use with a fingertip. The cap 200 can also be adjusted for the desired or required penetration depth of the lancet 222 with movement of the cap body 202 via the second cam path 216 and cam follower 218.

Referring to FIGS. 3A-5B, the cap 200 is shown in the finger mode. In finger mode, the lancet receiver 208 is in a forward position, so that an end 228 of the lancet receiver 208 is interposed in or obstructs a portion of the piercing aperture 206, providing in conjunction with the skin-engaging end 204, a skin-engaging contour that is suitable for placement against a finger. The obstruction of the piercing aperture 206 that is effected by the lancet receiver 208 need not be complete; rather the receiver 208 can be placed in proximity to the piercing aperture 206 so that the user's skin will encounter the lancet receiver 208 when the cap 200 is placed against the user's body prior to firing the lancing device, and consequently, the user's skin will not be able to pucker into the cap 200 through piercing aperture 206, at least to the same extent as the skin could pucker if the lancet receiver 208 was not obstructing piercing aperture 206. When the lancet receiver 208 obstructs the piercing aperture 206, the end 228 of receiver 208 can be substantially coplanar with skin-engaging end 204. In other words, when the lancet receiver 208 is interposed within the piercing aperture 206, it adjusts the effective size of the piercing aperture 206 to the smaller diameter of the end 228 of the lancet receiver 208.

Referring to FIGS. 6A-8B, the cap 200 is shown in an AST mode. In AST mode, the lancet receiver 208 is positioned sufficiently spaced apart from the piercing aperture 206 to permit skin to pucker through the piercing aperture 206 during lancing when in the rearward position. The cap 200 is placed against a fleshy part of the body other than the fingertip. The skin-engaging end 204 engages the user's skin, causing it to pucker inside the relatively wide piercing aperture 206. The puckered flesh is then pierced by the lancet's sharp tip 230, allowing the user to apply pressure before, during and after lancing to help with blood acquisition. Clearance prevents wicking of the blood drop and allows the user to see when sufficient blood has been acquired. In other words, when the lancet receiver 208 is withdrawn from the piercing aperture 206, it adjusts the effective size of the piercing aperture 206 to a larger diameter—in this embodiment, the diameter of unobstructed piercing aperture 206. This larger diameter is sufficiently large to allow the user's skin to pucker into the piercing aperture 206.

The cap 200 is also configured to adjust a penetration depth of the lancet 222 with axial movement of the cap body 202 relative to the housing 226. As mentioned above, when the lancet 222 is fully inserted into the lancet receiver 208, the end 224 of the lancet 222 will engage with a lancet firing mechanism (not shown) disposed within the housing 226. Once engaged, the lancet 222 is fixed in that position relative to the axis A of the housing until cocking and firing. With the position of the lancet 222 fixed, the depth to which the lancet 222 will penetrate the skin can be adjusted by moving the cap body 202 forward and rearward along the axis A. This penetration depth adjustment can be performed in both the finger mode, shown in FIGS. 3A-5B, and AST mode, shown in FIGS. 6A-8B. The penetration depth setting of the lancet 222 is at its maximum when the cap body 202 is moved furthest rearward, or is positioned closest to the housing 226 along the axis A. The penetration depth is at its minimum when the cap body 202 the forwardmost, or is positioned farthest from the housing 226 along axis A. The depth of penetration can be adjusted based on the user's comfort, the amount of blood required, the thickness of the user's skin, and the like.

In FIGS. 3A and 3B, the cap 200 is set to finger mode and maximum penetration depth. As seen in FIG. 3B, the lancet receiver 208 is in the forward position with the end 228 of the lancet receiver 208 circumscribed by and substantially coplanar with the skin engaging end 204. The cap body 202 is in the most rearward position, thereby reducing the overall length of the lancing device so that the lancet tip 230 protrudes the furthest through the piercing aperture 206. FIG. 3A shows the position of the actuating mechanism 220 looking down the longitudinal axis A.

Figure 9:
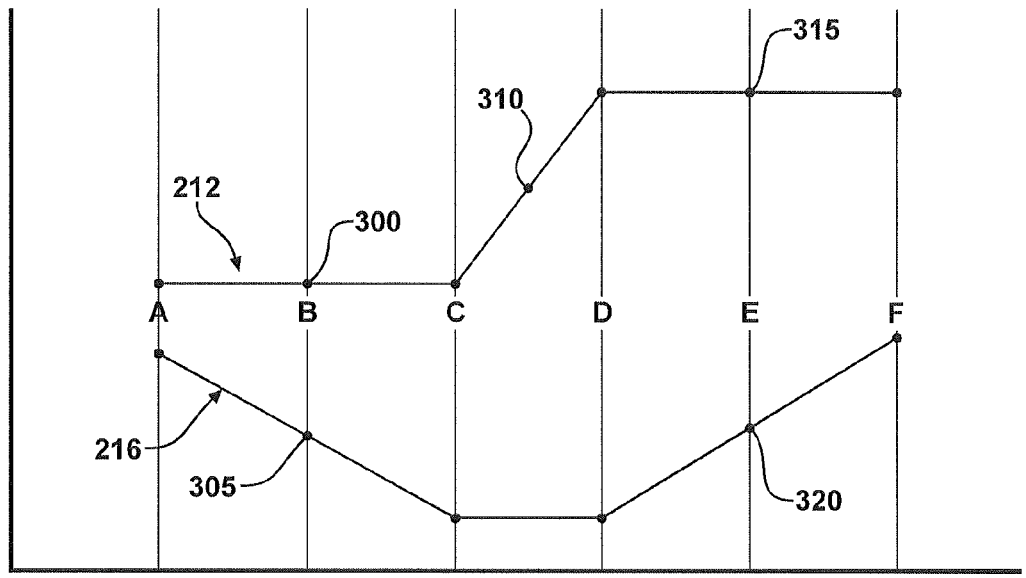
FIG. 9 is a schematic view depicting the cam paths of an embodiment disclosed herein.

Referring to FIG. 9, a schematic of the first and second cam paths 212, 216 is provided by way of explanation. The top path is the first cam path 212 in which the first cam follower 214 engages to move the lancet receiver 208 between the forward and rearward positions. The bottom path is the second cam path 216 in which the second cam follower 218 engages to move the cap body 202 forward and rearward to adjust penetration depth. The cap position shown in FIG. 3B is shown in FIG. 9 as point A. The lancet receiver 208 remains in the finger mode (shown as 300 in FIG. 9), or forward position, while the cap body 202 is moved with the actuating mechanism along the second cam path 216 to move the cap body 202 from its most rearward position closest to the housing 226 to a position away from the housing 226 and along path 305. This position is shown in FIG. 4B, and corresponds to point B in FIG. 9. FIG. 4A shows the relative position of the actuating mechanism 220 with this cap setting.

To further decrease the penetration depth of the lancet 222 while in finger mode, the actuating mechanism 220 can further move the second cam follower 218 along the second cam path 216, or path 305 in FIG. 9. At position C in FIG. 9, the cap 200 is set to finger mode and minimum penetration depth, meaning the cap body 202 is in its forward most position as shown in FIG. 5B. FIG. 5A shows the relative position of the actuating mechanism 220 with this cap setting.

If AST mode is desired or required, the user would continue to activate the actuating mechanism 220 to move the lancet receiver 208 from the forward position to the rearward position. The first cam follower 214 would move along path 310 in FIG. 9 until the lancet receiver 208 was in the rearward position, shown as 315. While the first cam follower 214 is moving along path 310, the cap body 202 does not move. At position D in FIG. 9, the cap 200 is positioned for AST mode and minimum penetration depth, shown in FIG. 6B. FIG. 6A shows the relative position of the actuating mechanism 220 with this cap setting.

While in AST mode, the penetration depth can be increased by moving the second cam follower 218 along the path segment 320 (seen in FIG. 9) of the second cam path 216. This cap setting, in AST mode with an intermediate penetration depth is shown in FIG. 7B and as position E in FIG. 9. FIG. 7A shows the relative position of the actuating mechanism 220 with this cap setting.

FIG. 8B shows the cap 200 in AST mode at the maximum penetration depth setting. This setting corresponds to position F in FIG. 9. FIG. 8A shows the relative position of the actuating mechanism 220 with this cap setting. At this point, the actuating mechanism 220 can be activated to move in the reverse, first keeping the first cam follower 214 in path segment 315 of the first cam path 212 and moving the second cam follower 218 along path segment 320 of second cam path 216. The reverse movement can be continued to move the lancet receiver 208 to the forward position for finger mode (300), and continuing to adjust depth penetration along path segment 305.

The positions A-F shown in FIG. 9 are meant as examples and are not meant to be limiting. It is contemplated that there are a plurality of stages or positions along the path segments 305 and 320 of the second cam path 216 so that depth penetration can be finely adjusted to many different settings within both the finger and AST modes.

The actuating mechanism 220 shown in the figures is a manually activated actuating mechanism in the form of a protrusion or lever. The actuating mechanism is user accessible to move the first and second cam followers 214, 218 along their respective cam paths 212, 216. The actuating mechanism 220 is not limited to this arrangement and can be any mechanism known to those skilled in the art that will function to move the cam followers. For example, the actuating mechanism 220 can be a slide button, an electrical mechanism, other mechanical mechanisms, a stepper motor, and the like.

The cap body 202 may be opaque (so that users do not see the sharp tip of the lancet), transparent, or colored and can provide protective closure around the lancet when the lancet is inserted into the lancet receiver 208. Although the cap body 202 may be constructed in a variety of sizes and configurations, in certain embodiments the piercing aperture 206 may be about 3 mm to about 15 mm in diameter and the skin-engaging surface 204 may have a width of about 1 mm to about 3 mm. The skin-engaging surface 204 can be circular or can have other shapes and need not be continuous or completely annular. The skin-engaging surface 204 may form a compression ring.

Although referred to as a skin-engaging surface, such surface does not have to actually come in contact with a user's skin. As non-limiting examples, there may be an intervening cover on the skin-engaging surface such as a non-slip or sterility coating or film. A deformable ring may be incorporated to form a seal on the tissue. There can be protrusions for stimulation or blood expression.

The cap 200 can be removed from the housing 226 to permit cleaning of the interior of the cap 200 and the lancet receiver 208, as well as the interior of the lancing device. To permit its removal, the cap body 202 can be threadably connected to housing 106 or connected via snap fit, for example. However, during operation of the lancing device it is not necessary to remove cap 200 as the device is loaded with the lancet 222 through the piercing aperture 206. It is also contemplated that the cap be permanently attached if desired or required.

In accordance with another embodiment of the invention, methods of use of a cap of a lancing device are disclosed. The cap 200 has a body 202, a skin-engaging end 204 defining a piercing aperture 206, an intermediate member 210 and a lancet receiver 208 movably disposed therein. Reference numbers are shown in FIGS. 3B-8B. One such method comprises adjusting an effective size of the piercing aperture 206 by moving the lancet receiver 208 between a forward position and a rearward position, wherein an end 228 of the lancet receiver 208 is circumscribed by and is substantially co-planar with the skin-engaging end 204 when the lancet receiver 208 is in the forward position, with the end 228 of the lancet receiver 208 defining the piercing aperture 206. The lancet receiver 208 is positioned sufficiently spaced apart from the piercing aperture 206 to permit skin to pucker through the piercing aperture 206 during lancing when in the rearward position.

Adjusting a penetration depth of a lancet 222 is accomplished by moving the cap body 202 forward and rearward when the lancet receiver 208 is in either of the forward and rearward positions. Adjusting the effective size comprises moving a first cam follower 214 located on one of the lancet receiver 208 and the intermediate member 210 with an actuating mechanism 220 along a first cam path 212 located on the other of the lancet receiver 208 and the intermediate member 210. Adjusting the penetration depth comprises moving a second cam follower 218 located on one of the cap body 202 and the intermediate member 210 with the actuation member 220 along a second cam path 216 on the other of the cap body 202 and the intermediate member 210. The first and second cam paths 212, 216 are shown in FIG. 9.

Figure 10:
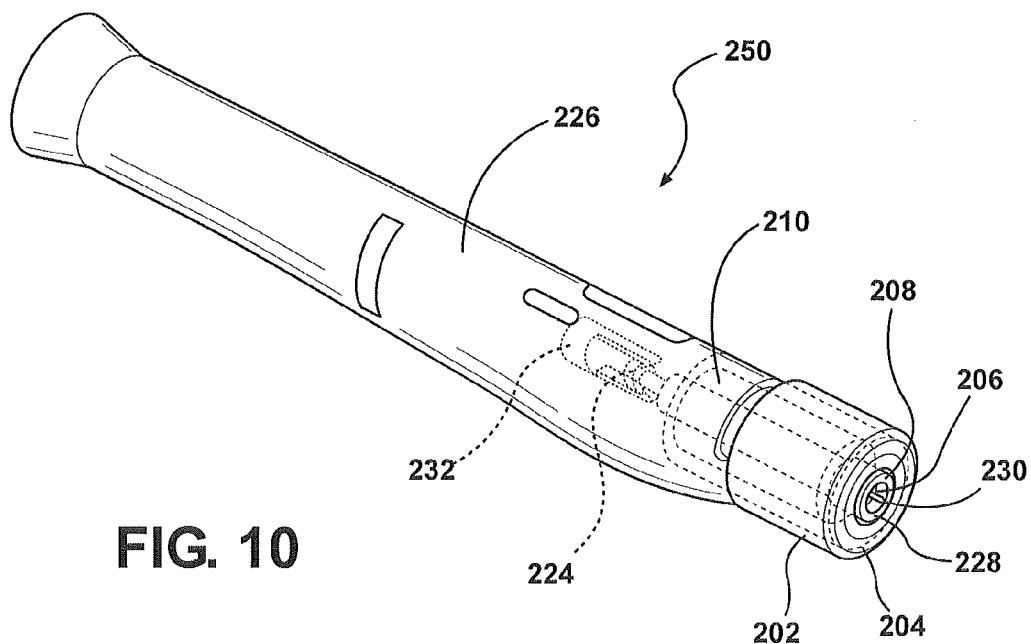
FIG. 10 is a perspective view depicting an embodiment of a lancing device disclosed herein.

In accordance with another embodiment of the invention, lancing devices are disclosed including a cap as described above. Referring to FIG. 10, like reference numbers refer elements previously described. The cap 200 has a body 202, a skin-engaging end 204 defining a piercing aperture 206, a lancet receiver 208 disposed in the cap body 202, an intermediate cap member 210, a housing 226 and a lancet firing mechanism 232 disposed in the housing 226. The lancing device 250 comprises a first cam path 212 on one of the lancet receiver 208 and the intermediate member 210, and a first cam follower 214 on the other of the lancet receiver 208 and the intermediate member 210 that engages the first cam path 212. A second cam path 216 is located on one of the cap body 202 and the intermediate member 210, and a second cam follower 218 is located on the other of the cap body 202 and the intermediate member 210 that engages the second cam path 216. The first and second cam paths 212, 216 are configured such that rotation of the intermediate member 210 by an actuating mechanism 220 causes the cap body 202 to move forward and rearward and the lancet receiver 208 to move forward and rearward. The first and second cam paths 212, 216 are schematically shown in FIG. 9. The cap position in FIG. 10 of lancing device 250 is maximum penetration depth in finger mode, equivalent to that shown in FIGS. 3A and 3B and position A on FIG. 9.

Although not shown, it is contemplated that any of the embodiments disclosed herein can include indicia on the outer circumferential surface of the cap and/or housing to indicate whether the cap is set to finger mode or AST mode and to indicate the penetration depth setting. For example, indicia can be a diagram of a human body, conveying to the user the fact that in AST mode bodily fluid can be drawn from tissue other than a finger. Lines of varying sizes may indicate the depth setting. Any descriptive symbols or icons may be used as desired or required.

The above-mentioned embodiments have been described in order to allow easy understanding of the present invention. The invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A cap for use with a lancing device having a housing and a lancet firing mechanism disposed therein, the cap comprising:
    a cap body having an inner surface and a skin-engaging end that defines a piercing aperture;
    a lancet receiver movably mounted in the cap body and having an outer surface, the lancet receiver configured to receive a lancet;
    an intermediate member movably mounted in the cap body and having an inner surface facing the outer surface of the lancet receiver;
    a first cam path on one of the outer surface of the lancet receiver and the inner surface of the intermediate member;
    a first cam follower on the other of the outer surface of the lancet receiver and the inner surface of the intermediate member that engages the first cam path;
    a second cam path on one of the inner surface of the cap body and an outer surface of the intermediate member;
    a second cam follower on the other of the inner surface of the cap body and the outer surface of the intermediate member that engages the second cam path; and
    an actuating mechanism attached to the intermediate member, wherein rotation of the intermediate member by the actuating mechanism causes the second cam follower to move along the second cam path to adjust a penetration depth of the lancet by moving the cap body forward and rearward with respect to the housing and causes the first cam follower to move along the first cam path to adjust an effective size of the piercing aperture by moving the lancet receiver forward and rearward with respect to the housing.

2. The cap of claim 1, wherein the lancet receiver is configured to move between a forward position and a rearward position, and wherein the cap body is configured to move forward and rearward when the lancet receiver is stationary in each of the forward position and the rearward position.

3. The cap of claim 2, wherein the lancet receiver is positioned sufficiently spaced apart from the piercing aperture to permit skin to pucker through the piercing aperture during lancing when in the rearward position.

4. The cap of claim 2, wherein an end of the lancet receiver is circumscribed by and is substantially co-planar with the skin-engaging end when the lancet receiver is in the forward position, the end of the lancet receiver defining the piercing aperture.

5. The cap of claim 2, wherein the cap body moves forward and rearward through a plurality of stages.

6. The cap of claim 1, wherein the lancet receiver is configured to receive the lancet through the piercing aperture such that the lancet engages the lancet firing mechanism and becomes fixedly secured in relation to the housing.

7. The cap of claim 1, wherein the lancet receiver is sized to permit insertion of the lancet therethrough while sufficiently narrow to prevent puckering of skin.

8. The cap of claim 1, wherein the actuating mechanism is one of a manual lever or a stepper motor.

9. The cap of claim 1 further comprising indicia indicating at least one of the position of the lancet receiver and the position of the cap body.

10. A method of use of a cap of a lancing device having a housing and a cap body with an inner surface and a skin-engaging end defining a piercing aperture, the method comprising:
a lancet receiver movably mounted in the cap body, wherein adjusting an effective size of the piercing aperture by moving the lancet receiver between a forward position and a rearward position, wherein an end of the lancet receiver is circumscribed by and is substantially co-planar with the skin-engaging end when the lancet receiver is in the forward position, with the end of the lancet receiver defining the piercing aperture, and the lancet receiver is positioned sufficiently spaced apart from the piercing aperture to permit skin to pucker through the piercing aperture during lancing when in the rearward position; and
adjusting a penetration depth of a lancet by moving the cap body forward and rearward when the lancet receiver is in either of the forward and rearward positions,
wherein the cap body has an intermediate member movably mounted in the cap body and having an inner surface facing an outer surface of the lancet receiver, an outer surface facing the inner surface of the cap body and an actuating mechanism attached to the intermediate member,
wherein adjusting the effective size comprises rotating the intermediate member with the actuating mechanism to move a first cam follower located on one of the outer surface of the lancet receiver and the inner surface of the intermediate member along a first cam path located on the other of the outer surface of the lancet receiver and the inner surface of the intermediate member to move the lancet receiver forward and rearward with respect to the housing, and
wherein adjusting the penetration depth comprises rotating the intermediate member with the actuation member to move a second cam follower located on one of the inner surface of the cap body and the outer surface of the intermediate member along a second cam path on the other of the inner surface of the cap body and the outer surface of the intermediate member such that the cap body moves forward and rearward relative to the housing at a different time than the lancet receiver.

11. The method of claim 10 further comprising:
receiving indication of at least one of the position of the lancet receiver and the position of the cap body from indicia located on the cap body.

12. The method of claim 10, wherein the lancet receiver is sized to permit insertion of the lancet therethrough while sufficiently narrow to prevent puckering of skin.

13. The method of claim 10, wherein the actuating mechanism is one of a manual lever or a stepper motor.

14. A cap for a lancing device including a housing and a lancet firing mechanism disposed in the housing, the cap comprising:
a cap body with a skin-engaging end defining a piercing aperture;
a lancet receiver movably disposed in the cap body;
an intermediate member movably disposed between the lancet receiver and the cap body;
a first cam path and a first cam follower movably connecting the lancet receiver and the intermediate member;
a second cam path and a second cam follower movably connecting the cap body and the intermediate member; and
an actuating mechanism accessible external to the cap body and carried by the intermediate member, wherein rotation of the intermediate member by the actuating mechanism causes the second cam follower to move along the second cam path to adjust a penetration depth of a lancet by moving the cap body forward and rearward relative to the housing and causes the first cam follower to move along the first cam path to adjust an effective size of the piercing aperture by moving the lancet receiver forward and rearward relative to the housing.

15. The lancing device of claim 14, wherein the lancet receiver is configured to move between a forward position and a rearward position, and wherein the cap body is configured to move forward and rearward when the lancet receiver is stationary in each of the forward position and the rearward position.

16. The lancing device of claim 15, wherein the lancet receiver is positioned sufficiently spaced apart from the piercing aperture to permit skin to pucker through the piercing aperture during lancing when in the rearward position, and wherein an end of the lancet receiver is circumscribed by and is substantially co-planar with the skin-engaging end when the lancet receiver is in the forward position, the end of the lancet receiver defining the piercing aperture.

17. The lancing device of claim 14, wherein the lancet receiver is configured to receive a lancet through the piercing aperture such that the lancet engages the lancet firing mechanism and becomes fixedly secured in relation to the housing.

18. The lancing device of claim 14, wherein the cap body moves forward and rearward through a plurality of stages.

19. The lancing device of claim 14, wherein the actuating mechanism is one of a manual lever or a stepper motor.

20. The lancing device of claim 14 further comprising indicia indicating at least one of the position of the lancet receiver and the position of the cap body.

* * * * *